United States Patent
Morningstar

(12) 
(10) Patent No.: US 8,337,392 B2
(45) Date of Patent: Dec. 25, 2012

(54) PENILE PROSTHETIC WITH ANTI-AUTOINFLATION MECHANISM

(75) Inventor: Randy L. Morningstar, Brooklyn Park, MN (US)

(73) Assignee: Coloplast A/S, Humlebaek (DK)

(*) Notice: Subject to any disclaimer, the term of this patent is extended or adjusted under 35 U.S.C. 154(b) by 127 days.

(21) Appl. No.: 12/887,513

(22) Filed: Sep. 22, 2010

(65) Prior Publication Data
US 2011/0118540 A1    May 19, 2011

Related U.S. Application Data

(60) Provisional application No. 61/261,760, filed on Nov. 17, 2009.

(30) Foreign Application Priority Data

Nov. 16, 2009 (DK) ................................ 2009 70206

(51) Int. Cl.
*A61F 5/00* (2006.01)
(52) U.S. Cl. ........................................................ 600/40
(58) Field of Classification Search .................. 128/897, 128/898; 600/38–41
See application file for complete search history.

(56) References Cited

U.S. PATENT DOCUMENTS

| | | | |
|---|---|---|---|
| 3,734,258 A | 5/1973 | Roob | |
| 3,853,122 A | 12/1974 | Strauch et al. | |
| 3,954,102 A | 5/1976 | Buuck | |
| 4,224,934 A | 9/1980 | Scott et al. | |
| 4,335,714 A | 6/1982 | Edgerton et al. | |
| 4,342,308 A | 8/1982 | Trick | |
| 4,353,360 A | 10/1982 | Finney et al. | |
| 4,360,010 A | 11/1982 | Finney | |
| 4,364,379 A | 12/1982 | Finney | |
| 4,441,491 A | 4/1984 | Evans, Sr. | |
| 4,453,411 A * | 6/1984 | Shikasho | 73/709 |
| 4,545,081 A | 10/1985 | Nestor et al. | |
| 4,559,931 A | 12/1985 | Fischell | |
| 4,566,446 A | 1/1986 | Fogarty | |

(Continued)

FOREIGN PATENT DOCUMENTS

WO    9804214    2/1998

(Continued)

OTHER PUBLICATIONS

Office Action from DK Patent Office.

*Primary Examiner* — Samuel Gilbert
(74) *Attorney, Agent, or Firm* — Coloplast Corp., Coloplast A/S; Daniel G. Chapik; Nicholas R. Baumann

(57) ABSTRACT

A pump connected to a body implantable penile prosthesis including a reservoir maintaining a fluid volume that is transferrable into a cylinder of the penile prosthesis is described. The pump includes a pump bulb connected to a pump body that is in fluid communication with the reservoir and the cylinder; an inlet valve operable to allow a portion of the fluid volume to be drawn from the reservoir and delivered into the pump bulb; an exhaust valve operable to allow the portion of the fluid volume delivered into the pump bulb to be pumped into the cylinder; and an anti-autoinflation (AAI) valve disposed in the pump body and comprising a seal that is biased to prevent fluid flow from bypassing the pump bulb and flowing from the reservoir to the cylinder.

6 Claims, 8 Drawing Sheets

U.S. PATENT DOCUMENTS

| | | |
|---|---|---|
| 4,572,168 A | 2/1986 | Fischell |
| 4,596,242 A | 6/1986 | Fischell |
| 4,846,909 A | 7/1989 | Klug et al. |
| 5,062,417 A | 11/1991 | Cowen |
| 5,067,485 A | 11/1991 | Cowen |
| 5,133,923 A | 7/1992 | Klug |
| 5,141,509 A | 8/1992 | Burton et al. |
| 5,159,920 A | 11/1992 | Condon et al. |
| 5,160,341 A | 11/1992 | Brenneman et al. |
| 5,167,611 A | 12/1992 | Cowan |
| 5,188,596 A | 2/1993 | Condon et al. |
| 5,250,020 A | 10/1993 | Bley |
| 5,263,946 A | 11/1993 | Klug |
| 5,454,798 A | 10/1995 | Kubalak et al. |
| 5,558,829 A | 9/1996 | Petrick |
| 5,584,271 A | 12/1996 | Sakata |
| 5,632,777 A | 5/1997 | Petrick |
| 5,653,757 A | 8/1997 | Petrick |
| 5,704,895 A | 1/1998 | Scott et al. |
| 5,725,507 A | 3/1998 | Petrick |
| 5,779,964 A | 7/1998 | Welch et al. |
| 5,851,176 A | 12/1998 | Willard |
| 5,895,424 A | 4/1999 | Steele, Sr. et al. |
| 5,919,170 A | 7/1999 | Woessner |
| 5,935,362 A | 8/1999 | Petrick |
| 6,039,750 A | 3/2000 | Kubalak et al. |
| 6,060,639 A | 5/2000 | Petrick |
| 6,171,233 B1 | 1/2001 | Willard |
| 6,443,887 B1 | 9/2002 | Derus et al. |
| 6,533,719 B2 | 3/2003 | Kuyava et al. |
| 6,537,192 B1 | 3/2003 | Elliott et al. |
| 6,572,527 B2 | 6/2003 | Steele, Sr. et al. |
| D476,471 S | 7/2003 | Alfaro |
| 6,599,231 B1 | 7/2003 | Hoedeman et al. |
| 6,616,593 B1 | 9/2003 | Elliott et al. |
| 6,638,211 B2 | 10/2003 | Suslian et al. |
| 6,639,237 B2 | 10/2003 | Pedersen et al. |
| 6,656,107 B1 | 12/2003 | Pedersen et al. |
| 6,682,471 B2 | 1/2004 | Steele, Sr. et al. |
| 6,723,042 B2 | 4/2004 | Almli et al. |
| 6,730,017 B2 | 5/2004 | Waldack et al. |
| D496,727 S | 9/2004 | Kubalak et al. |
| D496,993 S | 10/2004 | Kubalak et al. |
| D497,205 S | 10/2004 | Kubalak et al. |
| 6,805,690 B2 | 10/2004 | Ogden et al. |
| 6,869,390 B2 | 3/2005 | Elliott et al. |
| 6,887,230 B2 | 5/2005 | Kubalak et al. |
| 6,895,998 B2 | 5/2005 | Aoki et al. |
| D508,128 S | 8/2005 | Kubalak et al. |
| 6,935,847 B2 | 8/2005 | Kuyava et al. |
| 6,953,426 B2 | 10/2005 | Barber et al. |
| 6,991,601 B2 | 1/2006 | Kuyava et al. |
| 7,001,307 B2 | 2/2006 | Matsunaga et al. |
| 7,066,878 B2 | 6/2006 | Eid |
| 7,229,400 B2 | 6/2007 | Elliott et al. |
| 7,244,227 B2 * | 7/2007 | Morningstar .................. 600/40 |
| 2002/0082473 A1 | 6/2002 | Henkel et al. |
| 2003/0065249 A1 | 4/2003 | Kuyava et al. |
| 2004/0220447 A1 | 11/2004 | Morningstar |
| 2004/0220448 A1 | 11/2004 | Henkel et al. |
| 2004/0225182 A1 | 11/2004 | Eid |
| 2004/0249397 A1 | 12/2004 | Delorme |
| 2004/0249473 A1 | 12/2004 | Delorme |
| 2005/0010945 A1 | 1/2005 | Hayashi |
| 2005/0027252 A1 | 2/2005 | Boukas |
| 2005/0028418 A1 | 2/2005 | Pargman |
| 2005/0075529 A1 | 4/2005 | Pedersen et al. |
| 2005/0131274 A1 | 6/2005 | Suslian |
| 2005/0209499 A1 | 9/2005 | Elliott et al. |
| 2005/0250981 A1 | 11/2005 | Kuyava et al. |
| 2005/0267320 A1 | 12/2005 | Barber |
| 2005/0278037 A1 | 12/2005 | Delorme |
| 2005/0288692 A1 | 12/2005 | Beraud |
| 2006/0003190 A1 | 1/2006 | Abarra et al. |
| 2006/0012252 A1 | 1/2006 | Miyata et al. |
| 2006/0025753 A1 | 2/2006 | Kubalak |
| 2006/0063960 A1 | 3/2006 | Wissman |
| 2006/0135845 A1 | 6/2006 | Kuyava et al. |
| 2006/0173468 A1 | 8/2006 | Simmon |
| 2006/0224039 A1 | 10/2006 | Steele |
| 2007/0135673 A1 | 6/2007 | Elliott et al. |
| 2007/0142700 A1 | 6/2007 | Fogarty et al. |

FOREIGN PATENT DOCUMENTS

| | | |
|---|---|---|
| WO | 2006066199 | 6/2006 |
| WO | 2007073556 | 6/2007 |

* cited by examiner

PENILE PROSTHETIC WITH ANTI-AUTOINFLATION MECHANISM

BACKGROUND

An implanted penile prosthetic is a proven approach to relieve erectile dysfunction for male users.

A penile prosthetic typically includes one or more cylinders that are implanted in the corpora cavernosa of the penis, a reservoir implanted in the abdomen that communicates with the cylinder(s), and a pump, often located in the scrotum, that is employed to move liquid from the reservoir into the cylinder(s).

In a typical application, the user squeezes a bulb of the pump multiple times to draw liquid out of the reservoir into the bulb and thereafter transfer the liquid from the bulb into the cylinder(s). Squeezing the bulb thus inflates the cylinder(s) to provide the user with an erect penis. The user may return the penis to its flaccid state by selectively transferring the liquid from the cylinder(s) back into the reservoir.

The above-described penile prosthetics can experience autoinflation. Autoinflation occurs when the reservoir pressure increases, for example when the user bends or leans against a hard surface, which results in the reservoir being compacted or squeezed by the pubic bone, as one example. In this case the pressurized liquid in the reservoir is forced directly into the cylinder, thus creating an unintended and undesirable erection of the penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
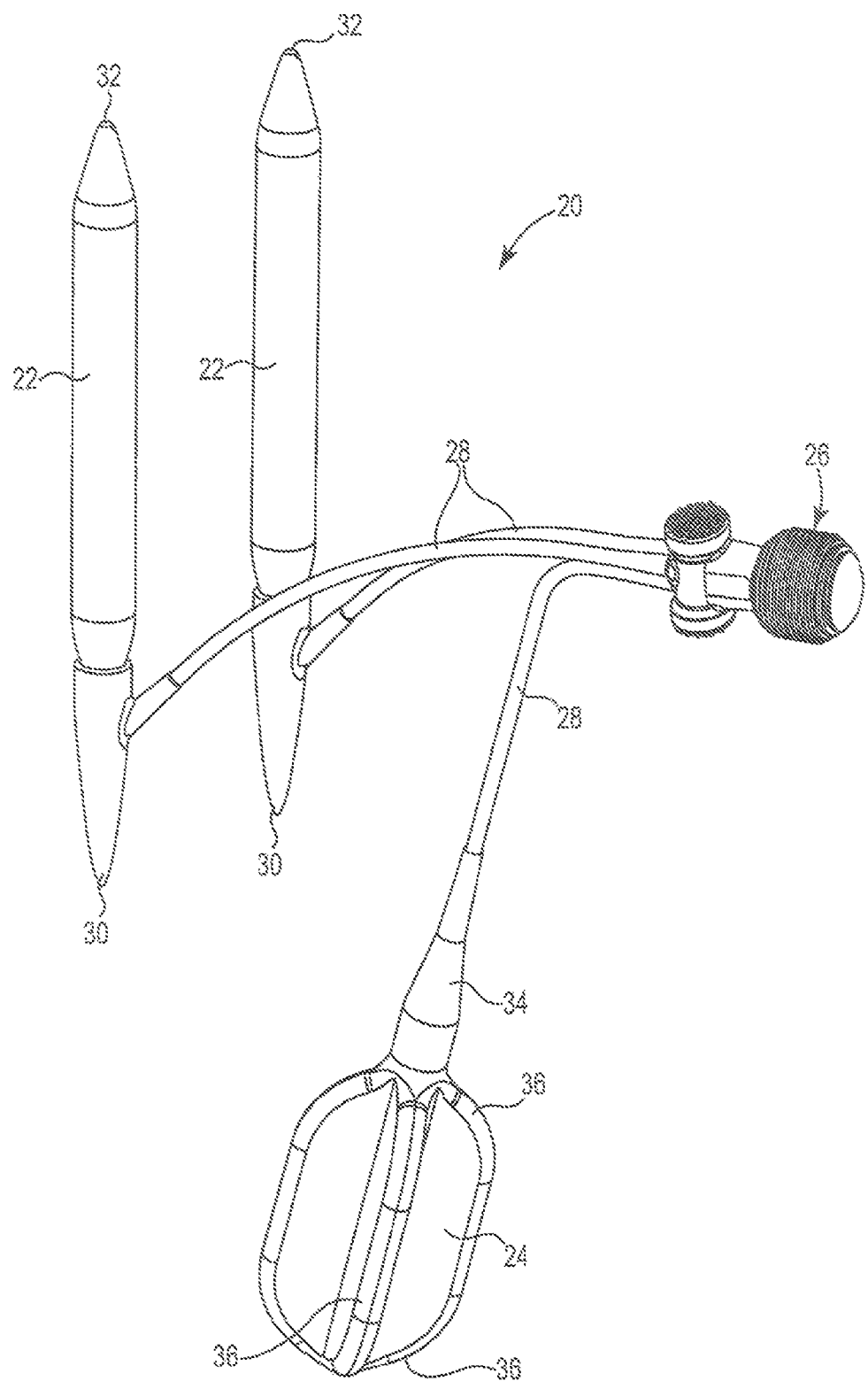
FIG. 1 is a perspective view of a penile prosthetic that includes cylinders for implantation into the penis, a reservoir, and a pump connected to the cylinders and the reservoir according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense.

It is to be understood that the features of the various exemplary embodiments described herein may be combined with each other, unless specifically noted otherwise.

The term "proximal" as employed in this application means that part that is situated next to or near the point of attachment or origin or a central point: as located toward a center of the human body. The term "distal" as employed in this application means that part that is situated away from the point of attachment or origin or the central point: as located away from the center of the human body. A distal end is the furthest endmost location of a distal portion of a thing being described, whereas a proximal end is the nearest endmost location of a proximal portion of the thing being described.

"Autoinflation" means an involuntary inflation of a cylinder implanted in a penis. Autoinflation occurs when the pressure of the liquid inside a reservoir that supplies the cylinder is increased, and the increased pressure forces liquid from the reservoir into the cylinder. The consequence is an unintended and undesirable erection of the penis.

Existing penile prosthetics can experience autoinflation in which the fluid stored in the reservoir can and will bypass the pump bulb and flow directly from the reservoir to the cylinder when the fluid pressure in the reservoir is increased. One solution to the undesired effects of autoinflation is to provide the reservoir with a one-way reservoir valve that resists pressure spikes in the reservoir to prevent unintentional liquid flow out of the reservoir while allowing intentional pumping of the pump bulb to draw the liquid past the one-way reservoir valve. The one-way reservoir valve adds bulk to the reservoir, which can create challenges for the surgeon implanting the reservoir, and can possibly lead to discomfort for the user. In addition, the one-way reservoir valve is vulnerable to unintended deactivation since the reservoir is implanted in the abdomen, which is an area of the body that can be subjected to bending and/or compression forces prevalent during activity or sneezing and the like. Active users of such penile prosthetics have reported autoinflation due to inadvertent deactivation of the one-way reservoir valve.

Embodiments provide a penile prosthetic provided with a pump having an anti-autoinflation (AAI) mechanism. The pump includes a pump bulb and a pump body. The pump body extends from the pump bulb and is connected to tubing that communicates with cylinders and a reservoir of the penile prosthetic. In one embodiment, the anti-autoinflation mechanism is provided as an AAI valve that is disposed in the pump body and has a seal that is biased to prevent fluid flow from bypassing the pump bulb and flowing directly from the reservoir to the cylinders. In this manner, pressure spikes delivered to the reservoir (for example by sneezing or external pressure sources) are blocked by the AAI valve to prevent unintended inflation of the cylinders.

FIG. 1 is a perspective view of penile prosthetic 20 according to one embodiment. The penile prosthetic 20 includes cylinders 22 for implantation into a penis, a reservoir 24, and a pump 26 connected to the cylinders 22 and the reservoir 24, for example by kink resistant tubing 28.

Each of the cylinders 22 includes a proximal end 30 opposite a distal end 32. During implantation, the proximal end 30 (also called a rear tip) is implanted toward the crus of the penis and the distal end 32 is implanted within the glans penis. The cylinders 22 are fabricated from material configured to collapse and be flexible when the cylinders 22 are deflated to provide the penis with a flaccid state and expand when the cylinders 22 are inflated with fluid to provide the penis with an erection. As a point of reference, the cylinders 22 of FIG. 1 are illustrated in an inflated state. Suitable material for fabricating the cylinders 22 includes silicone, biocompatible polymers such as urethanes, blends of polymers with urethane, copolymers of urethane, or the like. Suitable cylinders are available from Coloplast Corp., Minneapolis, Minn.

The reservoir 24 is sized to maintain a volume of liquid between about 50-300 ml and includes a neck 34 that is smoothly coupled with the kink resistant tubing 28. In one embodiment, the reservoir 24 is provided as a "cloverleaf" style of reservoir having multiple leaves that may be folded one against the other to compact the reservoir 24 for implantation into the abdomen of the user. One suitable reservoir 24 is sized to retain approximately 130 mL of liquid and is available from Coloplast Corp., Minneapolis, Minn.

Figure 2:
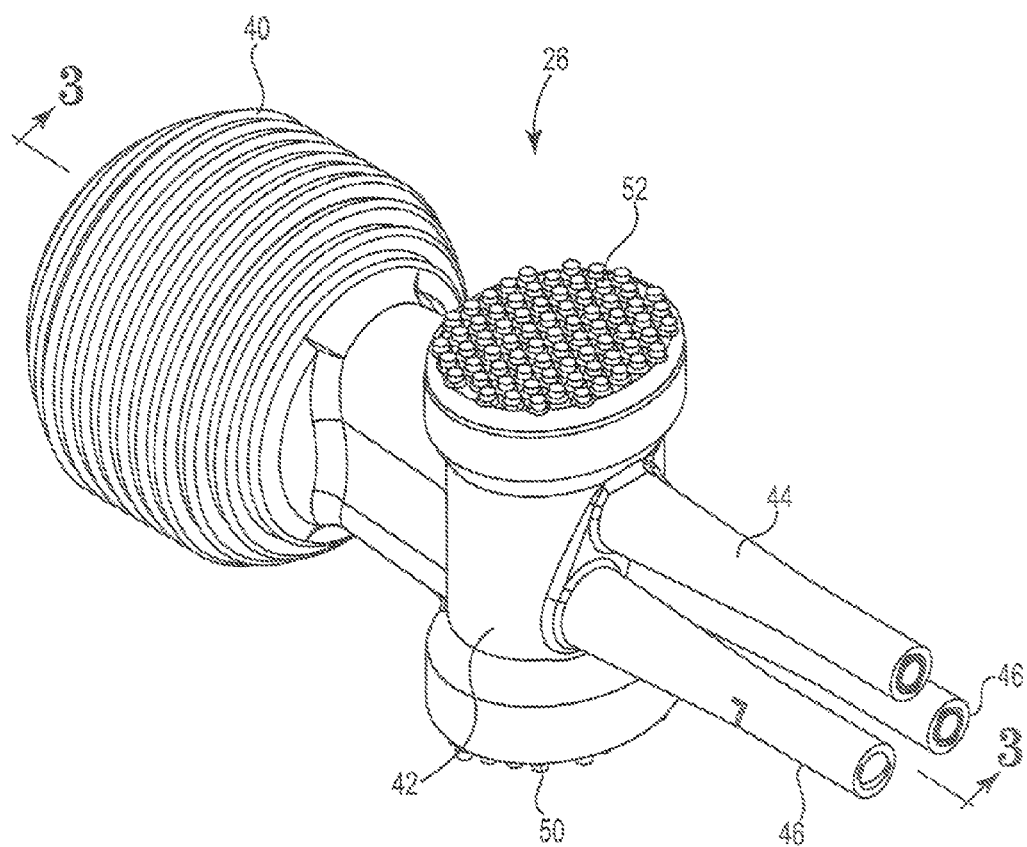
FIG. 2 is a perspective view of the pump illustrated in FIG. 1.

FIG. 2 is a perspective view of the pump 26. The pump 26 includes a pump bulb 40, a pump body 42, an inlet tube 44 connected with the pump body 42, and a pair of exhaust tubes 46 extending from the pump body 42.

In one embodiment, the pump bulb 40 is flexible and includes a pleated accordion structure that allows the pump bulb 40 to collapse to drive liquid out of the pump bulb 40, through the pump body, and out of the exhaust tubes 46. The pleated accordion structure is configured to recover to expand the bulb 40, which creates a negative local pressure in the bulb 40 that draws liquid out of the reservoir 24 (FIG. 1), through the inlet tube 44 and the pump body 42, and into the pump bulb 40.

In one embodiment, the pump body 42 is integrally formed and connected with the pump bulb 40 and includes a first activation surface 50 opposite a second activation surface 52. The activation surfaces 50, 52 are illustrated as non-circular (elliptical) although other shapes for the activation surfaces 50, 52 are also acceptable. The pump body 42 houses or maintains valves (described below) that may be activated/deactivated by pressing one or both of the activation surfaces 50, 52.

The inlet tube 44 is connected to the reservoir 24 (FIG. 1) by the kink resistant tubing 28. Each of the exhaust tubes 46 is connected to a respective one of the cylinders 22 via the kink resistant tubing 28. Compressing the pump bulb 40 ejects the liquid from the bulb 40 through the exhaust tubes 46 to the cylinders 22, and expansion of the pump bulb 40 creates suction that draws liquid from the reservoir 24 through the inlet tube 44 and the pump body 42 into the pump bulb 40.

Generally, the pump 26 is implanted into the scrotum of the user and connected to the cylinders 22 that are implanted into the penis of the user and the reservoir 24 that is implanted within the abdomen of the user. The pump 26 is fabricated from material suitable for body implantation, such as silicone or the urethane-based materials described above for the cylinders 22 or the reservoir 24.

Figure 3:
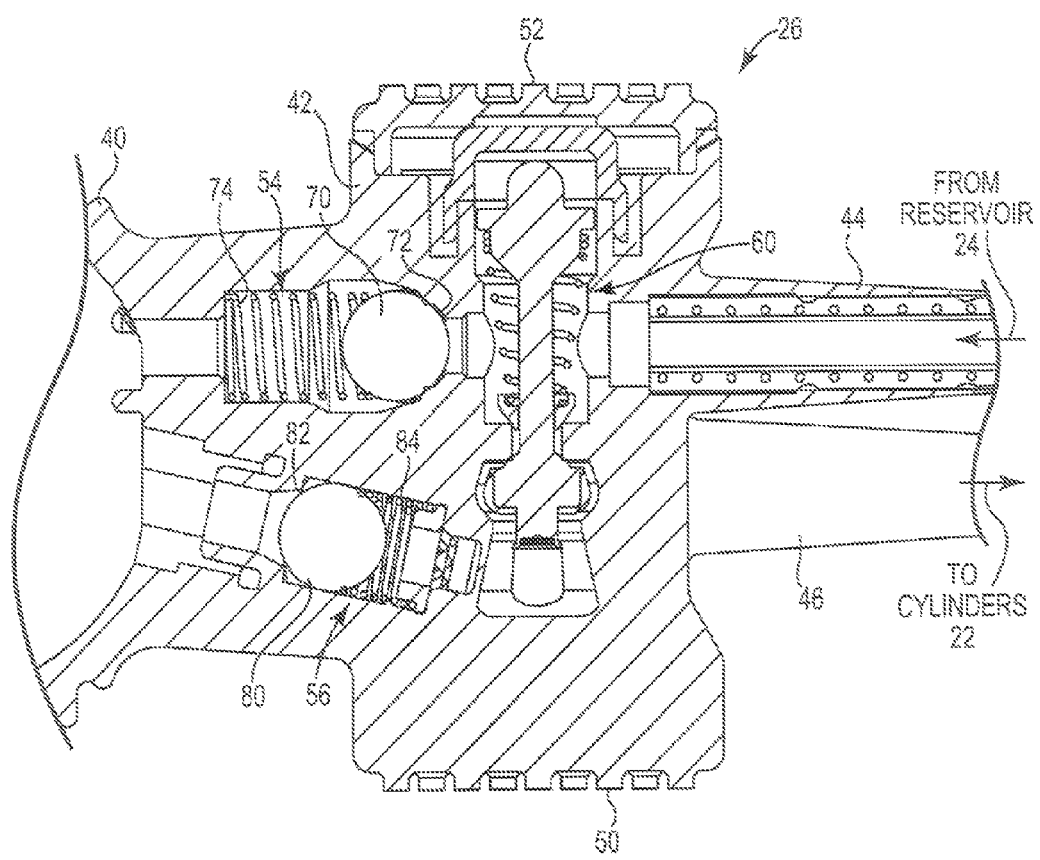
FIG. 3 is a cross-sectional view of an anti-autoinflation valve installed in a pump body of the pump illustrated in FIG. 2.

FIG. 3 is a cross-sectional view of the pump 26. The pump 26 includes an inlet valve 54 disposed within the pump body 42 that communicates between the reservoir 24 and the pump bulb 40, an exhaust valve 56 disposed within the pump body 42 that communicates between the pump bulb 40 and the cylinders 22, and an anti-autoinflation (AAI) valve 60 disposed in the pump bulb 42 transversely between the inlet valve 54 and the exhaust valve 56.

The inlet valve 54 includes a ball 70 that is biased into contact with a surface 72 by a spring 74. The ball 70 is configured to be displaced from the surface 72 (thus compressing the spring 74) when liquid flows from the reservoir 24 through the inlet tube 44 and into the pump bulb 40. When the liquid flow from the reservoir 24 is reduced, or more specifically, when the pressure driving the liquid flow from the reservoir 24 is reduced, the spring 74 biases the ball 70 into contact with the surface 72 to seat the ball on the surface 72 and block backflow of the liquid from the bulb 40 back to the reservoir 24. In this manner, the inlet valve 54 is provided as a one-way inlet valve.

The exhaust valve 56 includes a ball 80 that is biased into contact with a surface 82 by a spring 84. The ball 80 is configured to be displaced from the surface 82 (thus compressing the spring 84) when liquid flows from the pump bulb 40 through the exhaust valve 56 toward the cylinders 22. For example, compressing the pump bulb 40 ejects liquid from the pump bulb 40, which unseats the ball 80 from the surface 82 to allow the liquid to flow past the ball 80 and the AAI valve 60 into the cylinders 22. Expansion (or recovery) of the pump bulb 40 draws liquid from the reservoir 24, past the ball 80, and into the bulb 40. The spring 84 biases the ball 80 into contact with the surface 82 to block backflow of liquid from the cylinders 22 into the pump bulb 40. In this manner, the exhaust valve 56 is provided as a one-way exhaust valve.

Figure 5:
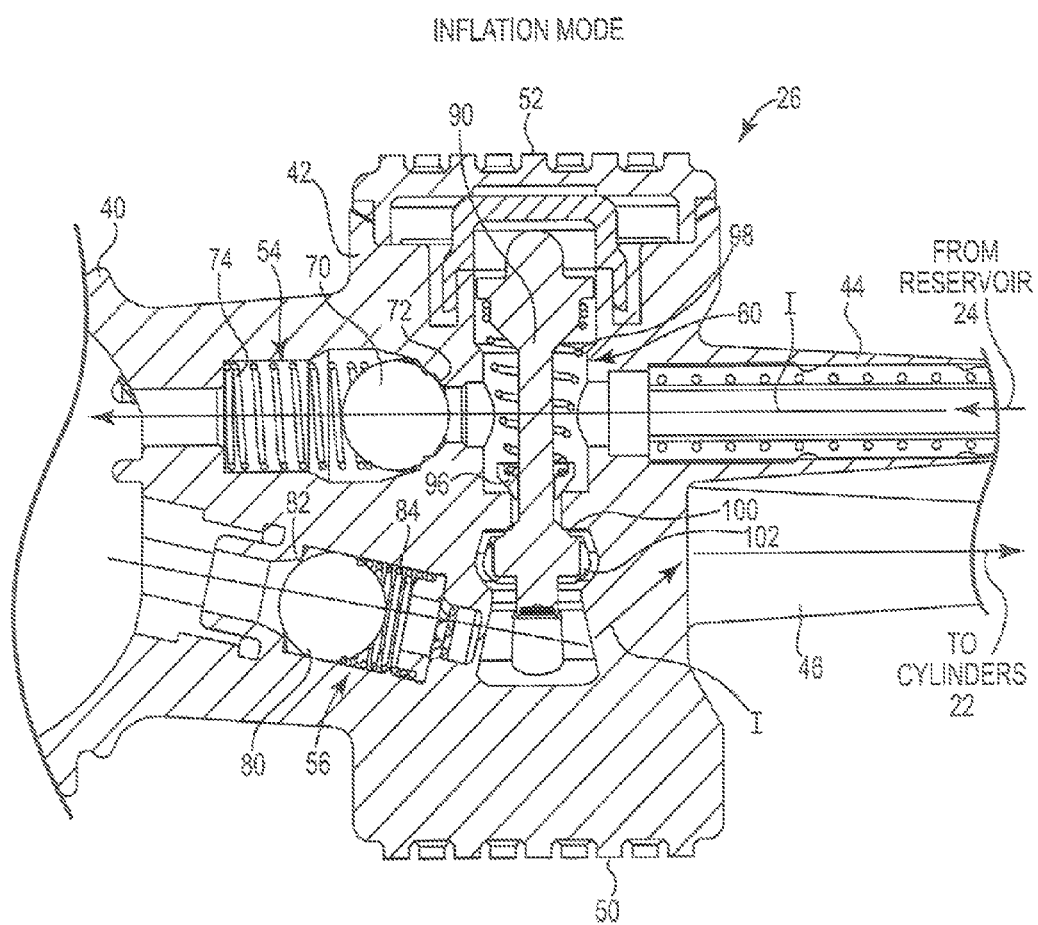
FIG. 5 is a cross-sectional view of the pump body with the anti-autoinflation valve configured for inflation of the cylinder.
Figure 6:
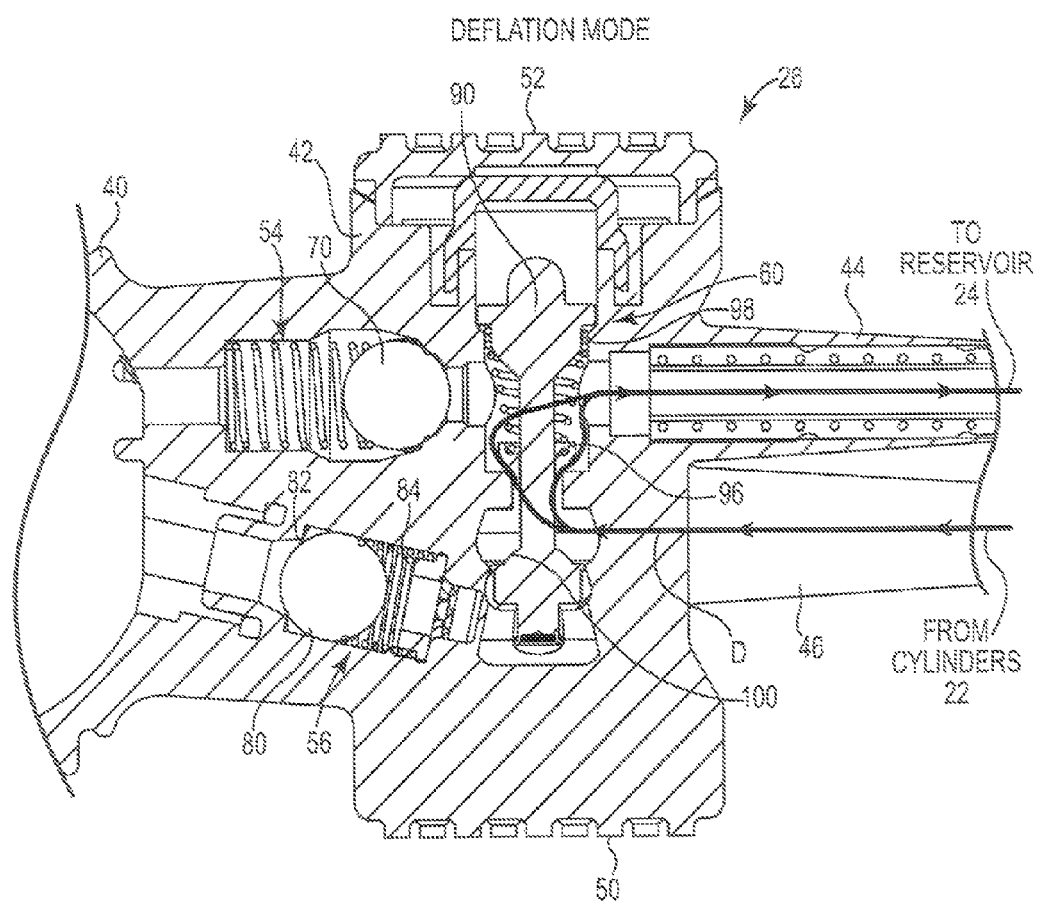
FIG. 6 is a cross-sectional view of the pump body with the anti-autoinflation valve configured for deflation of the cylinder.

In one embodiment, the pump body 42 is an elastomeric chamber molded around the AAI valve 60. The AAI valve 60 is configured to allow liquid to flow from the reservoir 24 into the pump bulb 40 and out the pump bulb 40 into the cylinders 22 during inflation of the cylinders (FIG. 5). The AAI valve 60 is also configured to allow for the rapid deflation of the cylinders 22 (FIG. 6). For example, in one embodiment pressing on the activation surface 52 positions the AAI valve 60 to allow fluid to flow from the cylinders 22 through the pump body 42, bypassing the pump bulb 40, and flowing directly back into the reservoir 24, as described below. In addition, the AAI valve 60 is configured to prevent undesirable autoinflation of the cylinders 22 by preventing fluid from flowing from the reservoir 24 directly into the cylinders 22, bypassing the pump bulb 40, as described more fully below.

Figure 4:
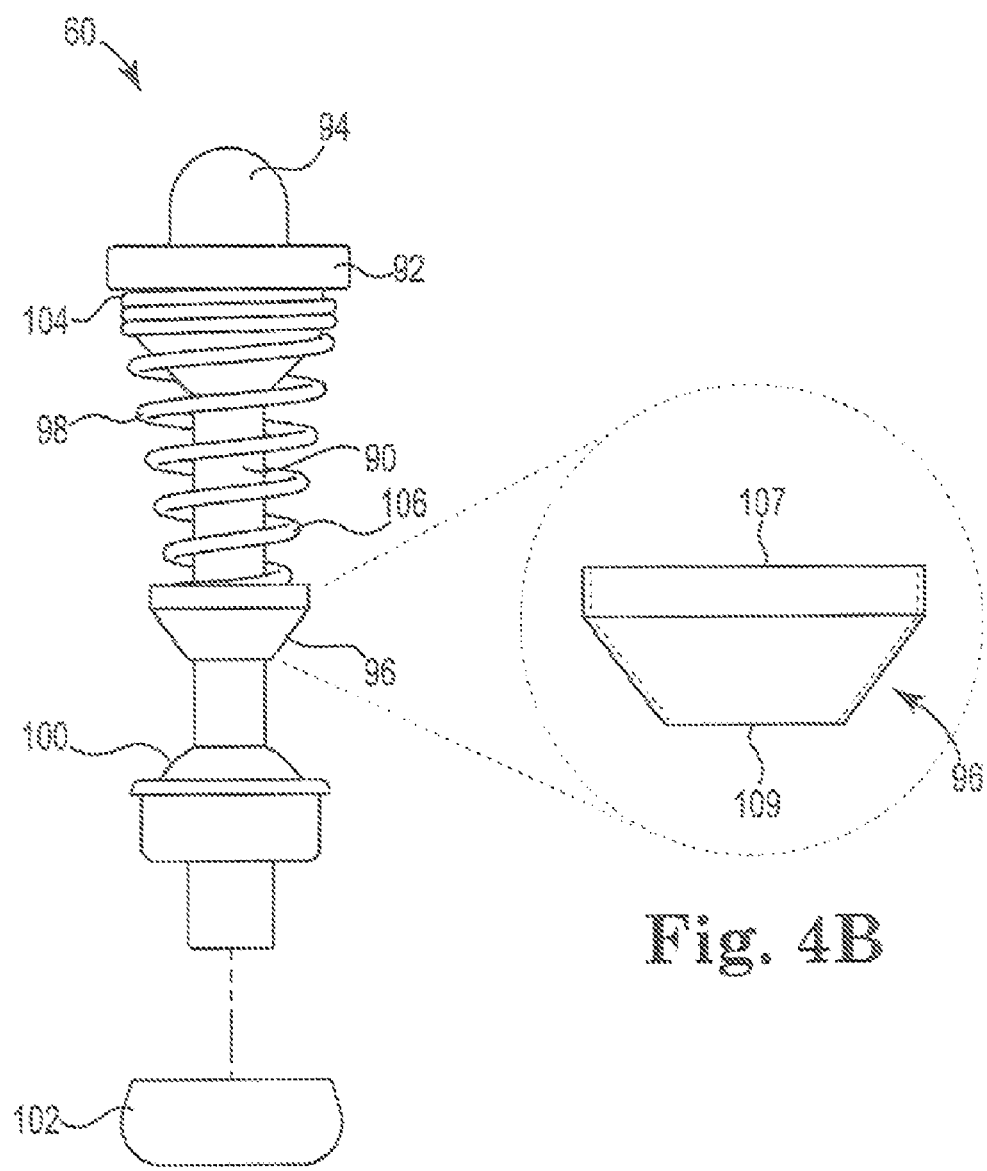
FIG. 4A is a side view of the anti-autoinflation valve according to one embodiment.
FIG. 4B is a side view of a seal of the anti-autoinflation valve illustrated in FIG. 4A.

FIG. 4A is a side view of the AAI valve 60. The AAI valve 60 includes a valve stem 90, a flange 92 disposed on a first end of portion 94 of the valve stem 90, a seal 96, a spring 98 that biases the seal 96 away from the flange 92 toward a second end portion 100 of the valve stem 90, and a crown 102 attached to the valve stem 90 opposite the flange 92. In one embodiment, the spring 98 is a conical spring having a base 104 that interacts with the flange 92 and an end 106 that interacts with the seal 96. The base 104 is wider than the end 106.

FIG. 4B is a side view of the seal 96. In one embodiment, the seal 96 is a conical seal having a wider end 107 oriented toward the flange 92 and a narrower end 109 oriented toward the second end portion 100. The conical spring 98 is mated into the wider conical end 107 of the seal 96. The wider end 107 is configured to block or deny the flow of liquid from the reservoir 24 transverse through the pump body 42 into the cylinders 22.

With reference to FIG. 3, the wider end 107 of the seal 96 of the AAI valve 60 is configured to be biased by the spring 98 to prevent fluid flow from bypassing the pump bulb 40 and flowing directly from the reservoir 24 into the cylinders 22 through the pump body 42. Any fluid that flows from the reservoir 24 through the pump body 42 toward the exhaust tubes 46 (i.e., autoinflation flow) forces the wider end 107 of the seal 96 toward the second end portion 100 of the valve stem 90 to close off the flow path in the direction of the exhaust tubes 46. In one embodiment, the second end portion 100 of the valve stem 90 seals the flow path through the pump body 42 during inflation of the cylinders 22 to prevent fluid that is flowing from the pump bulb 40 from being diverted through the pump body 42 to or toward the reservoir 24. In one embodiment, the crown 102 seals the flow path between the cylinders 22 and the pump bulb 40 during deflation of the cylinders 22 to ensure that the fluid being forced from the cylinders is diverted through the pump body 42 (away from the pump bulb 40) and back into the reservoir 24.

FIG. 5 is a cross-sectional view of the pump 60 with the AAI valve 60 configured for inflation of the cylinders 22 (i.e., AAI valve is in the inflation mode). With reference to FIG. 1, when the pump bulb 40 expands to create a vacuum, fluid is drawn from the reservoir 24 across the pump body 42 and into the pump bulb 40. The fluid moves through the inlet tubing 44 and through the inlet valve 54 along a pathway I. The ball 70 is displaced from its seat on surface 72 to allow the fluid to flow through the inlet valve 54 in into the pump bulb 40. The ball 70 is biased onto surface 72 by the spring 74. When the pump bulb 40 is compressed, the fluid in the pump bulb 40 flows through the exhaust valve 56 along the pathway I, displacing the ball 80 away from its seat on a surface 82. The fluid is ejected from the pump bulb 40 and flows along the pathway I under the crown 102 of the AAI valve 60, through the exhaust tubing 46 and to the cylinders 22.

In one embodiment, the inlet valve 54 is aligned axially between the pump bulb 40 and the inlet tubing 44, and the exhaust valve 56 is aligned axially between the pump bulb 40 and the exhaust tubing 46.

In one embodiment, when the pump bulb 40 is squeezed, fluid moving through the exhaust valve 56 forces the crown 102 of the AAI valve upward 60 to seal the AAI valve 60 and prevent the fluid that is flowing toward the cylinders 22 from being diverted through the pump body 42 toward the reservoir 24. Subsequent multiple pumps of the pump bulb 40 transfers the fluid in the reservoir 24 through the pump body 42, to the pump bulb 40, and out of the pump bulb 40 to the cylinders 22.

The AAI valve 60 is placed within the pump body 42 transversely between the inlet valve 54 and the exhaust valve 56. During inflation, the AAI valve 60 prevents the fluid flowing from the pump bulb 40 to the cylinders 22 from being diverted toward the reservoir 24. Specifically, the second end portion 100 of the valve stem 90 prevents fluid from flowing toward the reservoir 24 during inflation of the cylinders 22.

In some cases, the AAI valve 60 is configured to have an open state associated with the rapid deflation of the cylinders 22. In the open state, a first compression of the pump bulb 40 ejects fluid from the pump bulb 40 that impinges on the crown 102 to close the AAI valve 60. In one embodiment, the AAI valve 60 is a multi-functional valve that prevents flow to the reservoir 24 during cylinder inflation.

In one embodiment, the inlet valve 54 is minimally biased in the closed position so that it can open to allow fluid flow from the reservoir 24 to the pump bulb 40 as the pump bulb 40 rebounds. Pump bulb rebound causes a negative pressure on the inlet valve 54, usually less than 10 inches of mercury. The inlet valve 54 can open fully at negative pressures less than 10 inches of mercury. The inlet valve 54 cooperates with the primary valve seat 96/102 to prevent fluid from returning to the reservoir 24 when the pump bulb 40 is collapsed. In one embodiment, the inlet valve spring 74 is sized so that the inlet valve 54 remains open at low pressure (<10 inches of mercury) and closes at elevated pressures. In one embodiment, the inlet valve 54 is configured so that it remains open for a few seconds after the pump bulb 40 is collapsed to allow the pump bulb 40 to rebound and refill before closing. This is provided via a valve that shortens and then elongates within a few seconds time, e.g., a spring-loaded dashpot-type valve.

FIG. 6 is a cross-sectional view of the pump 26 with the AAI valve 60 configured for deflation of the cylinders 22 (i.e., AAI valve is in the deflation mode). The AAI valve 60 additionally allows for the rapid deflation of the cylinders 22 by providing a pathway D from the cylinders 22 back to the reservoir 24 that bypasses the pump bulb 40. In one embodiment, the activation surface 50 is pressed to dislodge the seal 96 from its seat inside of the pump body 42. Dislodging the seal 96 provides the liquid in the cylinders 22 with the pathway D through the pump body 42 that bypasses the pump bulb 40. When the activation surface 50 is pressed, the seal 96 is displaced upward (relative to the illustration of FIG. 6) to compress the spring 98 and allow fluid to move past the seal 96 along the pathway D and back to the reservoir 24. The ball 80 is seated against the surface 82 to prevent fluid flowing from the cylinders 22 back into the pump bulb 40. Thus, the path of least resistance for fluid leaving the cylinders 22 is across the unseated seal 96.

Figure 7:
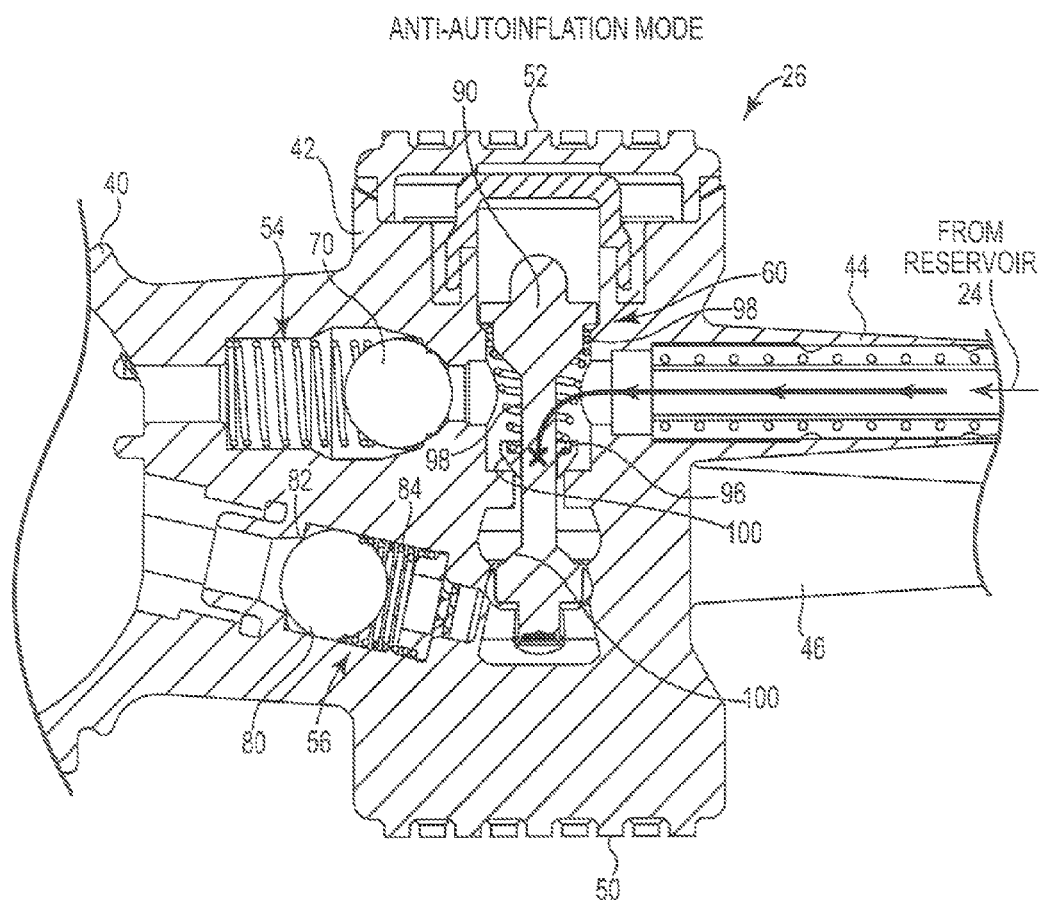
FIG. 7 is a cross-sectional view of the pump body with the anti-autoinflation valve actively preventing autoinflation of the cylinder.

FIG. 7 is a cross-sectional view of the pump 26 with the anti-autoinflation valve 60 (AAI valve 60) active to prevent autoinflation of the cylinders 22 (i.e., AAI valve is in the anti-autoinflation mode). Some physical activities can lead to the compression or pressurization of the reservoir 24. High reservoir pressure has the potential to cause fluid to flow from the reservoir 24 through the pump body 42 directly into the cylinders 22, potentially causing undesired autoinflation of the cylinders 22. The AAI valve 60 is configured to prevent autoinflation of the cylinders 22.

In one embodiment, the spring 98 the AAI valve 60 biases the seal 96 to close any potential fluid pathway from the reservoir 24 to the cylinders 22 that would bypasses the pump bulb 40. In one embodiment, the AAI valve is placed within the pump body 42 transversely relative to the inlet valve 54 and the exhaust valve 56 such that the seal 96 is biased by the spring 98 into contact with a mating surface 110 formed within the pump body 42. In one embodiment, the seal 96 is a conical seal having a greater surface area on the wide end 107 (FIG. 4B) that is oriented toward the reservoir 24, such that fluid flow from the reservoir 24 forces the seal 96 into sealing contact with the mating surface 110. In this manner, the AAI valve 60 is biased to prevent fluid flow from bypassing the pump bulb 40 and flowing directly from the reservoir 24 to the cylinders 22. In one embodiment, the AAI valve only allows fluid to be delivered to the cylinders 22 by pumping of the pump bulb 40.

In one embodiment, the seal 96 is movable and can be displaced or unseated from a mating surface 110 to allow rapid deflation of the cylinders 22, as described above with the pathway D in FIG. 6. The seal 96 is thus movable to allow fluid to flow transversely through the pump body 42 from the cylinders 22 to the reservoir 24 (e.g., deflation) and is configured to be biased to prevent the fluid from flowing transversely through the pump body from the reservoir 24 to the cylinders 22 (e.g., anti-autoinflation).

Figure 8:
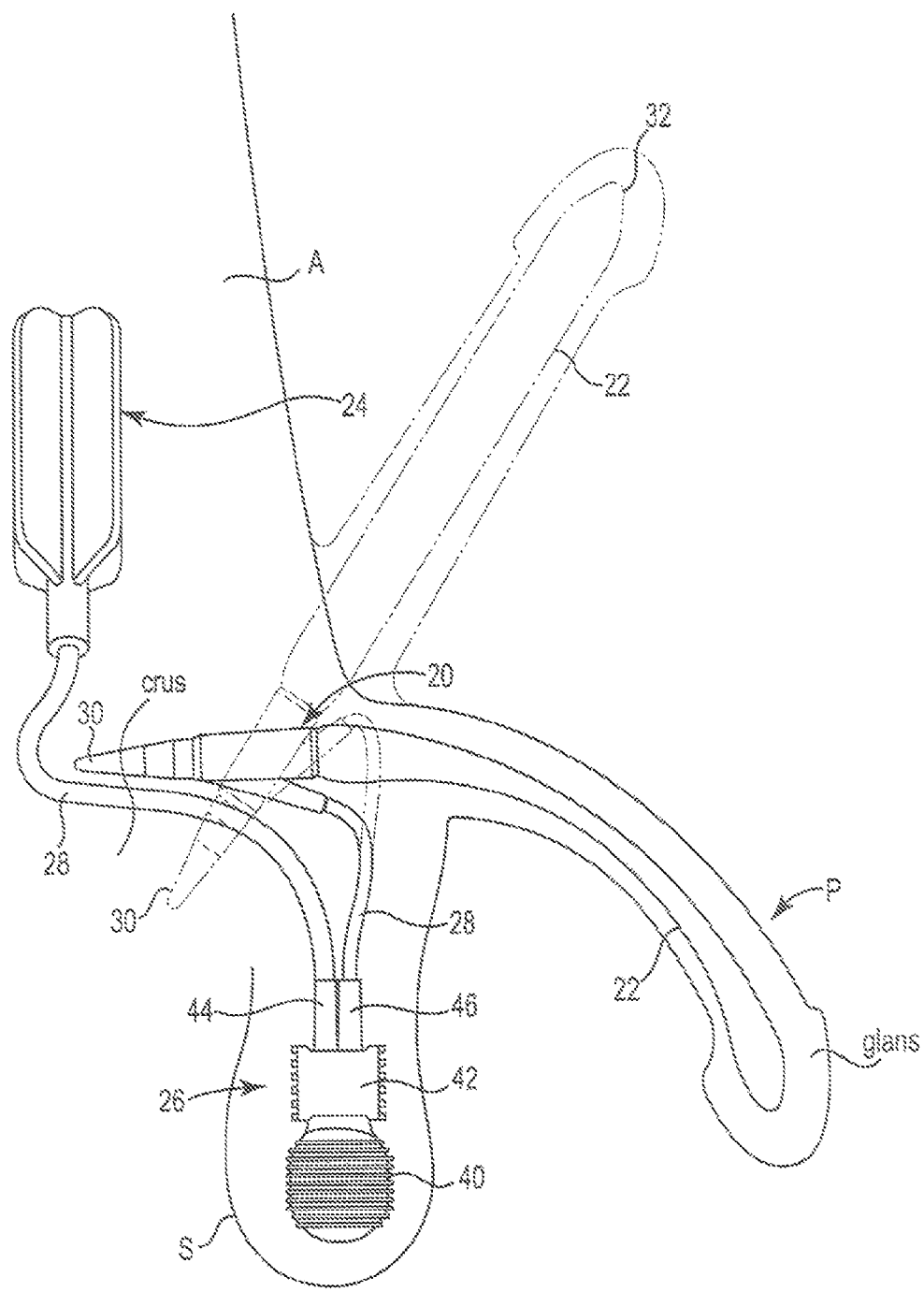
FIG. 8 is a schematic view of the penile prosthetic illustrated in FIG. 1 implanted into a user according to one embodiment.

FIG. 8 is a schematic side view of the penile prosthetic 20 implanted in a user. The cylinders 22 are implanted in the penis P with the proximal end 30 inserted near the crus and the distal end 32 implanted within the glans. The reservoir 24 is implanted within the abdomen A and the pump 26 is implanted within the scrotum S. The penile prosthetic 20 is operable consistent with the description above to inflate the cylinders 22 such that the penis P achieves an erect state (as described relative to FIG. 5). The cylinders 22 are configured to deflate to return the penis P to a flaccid state (as described relative to FIG. 6).

In one embodiment, a method of providing the inflatable penile prosthetic 20 includes connecting the pump body 42 to the reservoir 24, where the reservoir 24 is sized to maintain a fluid volume that is transferrable into the cylinder(s) 22, and configuring the pump body 42 to selectively inflate the cylinder(s) 22 of the penile prosthetic 20 with a portion of the fluid volume maintained in the reservoir 24. The method includes configuring the pump body 42 to include an anti-autoinflation mechanism that prevents the fluid volume from flowing from the reservoir 24 to the cylinder(s) 22 transversely through the pump body 42. Thus, the fluid in the reservoir 24 is prevented from undesirably autoinflating the cylinders 22.

In one embodiment, a method of preventing autoinflation of the penile prosthetic 20 includes connecting the pump body 42 to the reservoir 24, and sealing the pump body 42 to prevent fluid from flowing from the reservoir 24 transversely through the pump body 42 to the cylinder(s) 22 of the penile prosthetic 20.

In one embodiment, the pump 26 includes a one-touch release mechanism that allows the cylinders 22 to easily and quickly deflate by an initial, nearly instantaneous activation of one of the surfaces 50, 52 as opposed to the user applying prolonged pressure (e.g., more than three seconds of applied pressure) to the surfaces 50, 52. Thus, a quick and convenient approach is provided for the rapid deflation of the inflated cylinders 22.

In one embodiment, the inlet valve 54, exhaust valve 56, and AAI valve 60 have this sequence of inflation operation: The Penis P is flaccid and reservoir 24 is filled. The inlet valve 54 is closed, the exhaust valve 56 is closed, and the AAI valve 60 is closed. The pump bulb 40 is squeezed, the inlet valve 54 is closed, and the exhaust valve 56 opens to allow fluid flow and is biased closed to cease flow. The AAI valve 60 is closed and remains closed during subsequent pumping of the pump bulb 40, and fluid flows from the pump bulb 40 through the exhaust valve 56 to the penile cylinder(s) 22. When the pump bulb 40 is released during pumping action, the bulb volume expands to create suction and fluid is drawn from the reservoir 24 through the inlet valve 54 to the pump bulb 40, during which the exhaust valve is closed and the AAI valve 60 is closed until the bulb 40 is squeezed.

In one embodiment, the inlet valve 54, exhaust valve 56, and AAI valve 60 have this sequence of operations: The penis P is erect and the cylinder(s) 22 are filled. The inlet valve 54 is closed, the exhaust valve 56 is closed, and the AAI valve 60 is closed. The surface 50 is pushed, which unseats the seal 96 from the surface 110 (FIG. 7), and the liquid flows from the penile cylinder(s) 22 transversely through the AAI valve 60 and the pump body 42 to the reservoir 24 while the inlet valve 54 is closed and the exhaust valve 56 is closed.

In one embodiment, the inlet valve 54, exhaust valve 56, and AAI valve 60 have this sequence of operations: The penis P is flaccid and the reservoir 24 is filled with fluid. The inlet valve 54 is closed, the exhaust valve 56 is closed, and the AAI valve 60 is closed. The reservoir 24 is pressurized, either through a natural body function (e.g., sneezing) or through an external force (e.g., the user pressing against a table edge). The seal 96 of the AAI valve 60 remains closed and prevents fluid flow from bypassing the pump bulb 40 and flowing from the reservoir 24 to the cylinders 22.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein.

What is claimed is:

1. A pump connected to a body implantable penile prosthesis including a reservoir maintaining a fluid volume that is transferrable into a cylinder of the penile prosthesis, the pump comprising:
   a pump bulb connected to a pump body that is in fluid communication with the reservoir and the cylinder;
   an inlet valve operable to allow a portion of the fluid volume to be drawn from the reservoir and delivered into the pump bulb;
   an exhaust valve operable to allow the portion of the fluid volume delivered into the pump bulb to be pumped into the cylinder; and
   an anti-autoinflation (AAI) valve disposed in the pump body and comprising a valve stem and a seal attached to the valve stem, the seal located between the inlet valve and the exhaust valve and biased to prevent fluid flow from bypassing the pump bulb and flowing from the reservoir to the cylinder;
   wherein the AAI valve comprises the valve stem including a flange disposed on a first end portion, and a conical spring coupled axially to the valve stem between the flange and the seal, the conical spring configured to bias the seal away from the flange.

2. The pump of claim 1, wherein the seal of the AAI valve is conical with a first end that is wider than an opposing second end, the first end configured to block fluid from flowing through the pump body from the reservoir to the cylinder.

3. The pump of claim 2, wherein the conical seal is movable to allow fluid in the cylinder to flow past the second end of the seal, through the pump body, to the reservoir.

4. The pump of claim 1, wherein the AAI valve only allows fluid to be delivered into the cylinder via pumping of the pump bulb.

5. The pump of claim 1, wherein the inlet valve and the exhaust valve each comprises a one-way valve that communicates with the pump bulb, and the AAI valve is disposed transverse between the one-way inlet valve and the one-way exhaust valve.

6. A pump connected to a body implantable penile prosthesis including a reservoir maintaining a fluid volume that is transferrable into a cylinder of the penile prosthesis, the pump comprising:
   a pump bulb connected to a pump body that is in fluid communication with the reservoir and the cylinder;
   an inlet valve operable to allow a portion of the fluid volume to be drawn from the reservoir and delivered into the pump bulb;
   an exhaust valve operable to allow the portion of the fluid volume delivered into the pump bulb to be pumped into the cylinder; and
   an anti-autoinflation (AAI) valve disposed in the pump body and comprising a valve stem and a seal attached to the valve stem, the seal located between the inlet valve and the exhaust valve and biased to prevent fluid flow from bypassing the pump bulb and flowing from the reservoir to the cylinder;

wherein the inlet valve and the exhaust valve each comprises a one-way valve that communicates with the pump bulb, and the AAI valve is disposed transverse between the one-way inlet valve and the one-way exhaust valve.

* * * * *